(12) United States Patent
Arce et al.

(10) Patent No.: US 11,679,145 B2
(45) Date of Patent: *Jun. 20, 2023

(54) METHODS OF TREATING INFERTILITY

(71) Applicant: FERRING B.V., Hoofddorp (NL)

(72) Inventors: Joan-Carles Arce, Copenhagen (DK); Jane Ruman, Parsippany, NJ (US); Patrick Heiser, Parsippany, NJ (US)

(73) Assignee: FERRING B.V., Hoofddorp (NL)

( * ) Notice: Subject to any disclaimer, the term of this patent is extended or adjusted under 35 U.S.C. 154(b) by 256 days.

This patent is subject to a terminal disclaimer.

(21) Appl. No.: 17/117,643

(22) Filed: Dec. 10, 2020

(65) Prior Publication Data

US 2021/0093697 A1  Apr. 1, 2021

Related U.S. Application Data

(63) Continuation of application No. 16/555,688, filed on Aug. 29, 2019, now Pat. No. 11,351,228, which is a (Continued)

(30) Foreign Application Priority Data

Mar. 4, 2015 (EP) .................................. 15157661
Sep. 15, 2015 (EP) .................................. 15185191

(51) Int. Cl.
*A61K 38/24* (2006.01)
*A61B 17/425* (2006.01)
(Continued)

(52) U.S. Cl.
CPC ............ *A61K 38/24* (2013.01); *A61B 17/425* (2013.01); *A61K 45/06* (2013.01); *C12N 5/0604* (2013.01); *C12N 5/0609* (2013.01); *G01N 33/74* (2013.01)

(58) Field of Classification Search
CPC .......... A61K 38/24; A61B 17/425–435; A61D 19/00; A61D 19/04; C12N 5/0604;
(Continued)

(56) References Cited

U.S. PATENT DOCUMENTS

| 4,725,579 A | 2/1988 | Jones et al. |
| 10,413,592 B2 | 9/2019 | Arce et al. |

(Continued)

FOREIGN PATENT DOCUMENTS

| RU | 2466724 C1 | 11/2012 |
| WO | WO-00/63248 A2 | 10/2000 |

OTHER PUBLICATIONS

Amer et al., "The influence of circulating anti-Mullerian hormone on ovarian responsiveness to ovulation induction with gonadotrophins in women with polycystic ovarian syndrome: a pilot study," Reproductive Biology and Endocrinology, vol. 11, No. 1, pp. 115-125, Dec. 2013.
(Continued)

*Primary Examiner* — Thaddeus B Cox
(74) *Attorney, Agent, or Firm* — Foley & Lardner LLP

(57) ABSTRACT

The present invention relates to improved assisted reproductive technology using highly purified menotropin (HP-hMG) to stimulate follicle development in controlled ovarian stimulation, particularly in women at risk of a high ovarian response to controlled ovarian stimulation.

19 Claims, 2 Drawing Sheets

Study Design Flow Chart

Related U.S. Application Data continuation of application No. 15/053,116, filed on Feb. 25, 2016, now Pat. No. 10,413,592.

(60) Provisional application No. 62/121,131, filed on Feb. 26, 2015, provisional application No. 62/121,113, filed on Feb. 26, 2015.

(51) Int. Cl.
| | |
|---|---|
| *C12N 5/073* | (2010.01) |
| *A61K 45/06* | (2006.01) |
| *C12N 5/075* | (2010.01) |
| *G01N 33/74* | (2006.01) |

(58) Field of Classification Search
CPC ...... C12N 5/0609; G01N 33/74; G01N 33/76; A61P 15/08
See application file for complete search history.

(56) References Cited

U.S. PATENT DOCUMENTS

| | | |
|---|---|---|
| 2005/0020489 A1 | 1/2005 | Menezo |
| 2014/0235540 A1 | 8/2014 | Gleicher et al. |
| 2014/0349334 A1 | 11/2014 | Chavez et al. |
| 2020/0093893 A1 | 3/2020 | Arce et al. |

OTHER PUBLICATIONS

Arce et al., "Antimüllerian hormone in gonadotropin releasing-hormone antagonist cycles: prediction of ovarian response and cumulative treatment outcome in good-prognosis patients," Fertility and Sterility, vol. 99, No. 6, pp. 1644-1653, May 2013.

Ziebe et al., "Influence of ovarian stimulation with HP-hMG or recombinant FSH on embryo quality parameters in patients undergoing IVF," Human Reproduction, vol. 22, No. 9, pp. 2402-2413, Jun. 2007.

Devroey et al., "A randomized assessor-blind trial comparing highly purified hmG and recombinant FSH in a GnRH antagonist cycle with compulsory single-blastocyst transfer," Fertility and Sterility, vol. 97, No. 3, pp. 561-571, Mar. 2012.

International Search Report dated May 3, 2016 in application No. PCT/EP2016/053934.

Office Action dated Jul. 4, 2019 in Russian Application No. 2017131129/04(054343).

Search Report dated Jul. 2, 2019 in Russian Application No. 2017131129/04(054343).

Arce et al., "The rate of high ovarian response in women identified at risk by a high serum AMH level is influenced by the type of gonadotropin," GyneCol Endocrinol, (2014) 30(6): 444-450 (Published Nov. 2013).

Weghofer et al., "The impact of LH-containing gonadotropins on diploidy rates in preimpantation embryos: long protocol stimulation," Human Reproduction, vol. 23, No. 3, pp. 499-503 (2008).

Office Action dated Aug. 27, 2019 in Japanese Application No. 2017-545238.

METHODS OF TREATING INFERTILITY

CROSS-REFERENCE TO RELATED APPLICATIONS

This application is a continuation of U.S. application Ser. No. 16/555,688, filed Aug. 29, 2019 now U.S. Pat. No. 11,351,228), which is a continuation of U.S. application Ser. No. 15/053,116, filed Feb. 25, 2016 (now U.S. Pat. No. 10,413,592), which claims priority to U.S. Provisional Patent Application No. 62/121,113, filed Feb. 26, 2015; U.S. Provisional Patent Application No. 62/121,131 filed Feb. 26, 2015; European Patent Application No. 15157661, filed Mar. 4, 2015; and European Patent Application 15185191, filed Sep. 15, 2015, the contents of each of which are incorporated herein by reference in their entireties.

FIELD

The methods described herein relate to assisted reproductive technology. In particular, described herein are methods for treating infertility, including controlled ovarian stimulation methods that may be particularly useful for women at risk of a high ovarian response thereto.

BACKGROUND

Assisted reproductive technology (ART) procedures generally involve stimulating egg production, harvesting eggs from a woman's ovaries, combining them with sperm in vitro, and transferring them to a woman's uterus (the donor or another woman). Success of ART is hampered by maternal and perinatal risks associated with the stimulation of egg production, such as ovarian hyperstimulation syndrome (OHSS) and ectopic pregnancy. Other concerns that arise in ART are the production of quality embryos and euploid blastocysts to support ongoing pregnancy rates and live birth rates.

Gonadotropins, such as menotropin (e.g., human menopausal gonadotropin, or hMG), follicle-stimulating hormone (FSH) and luteinizing hormone (LH), have been widely used for controlled ovarian stimulation (COS), and highly purified menotropin (HP-hMG) and recombinant human FSH (r-hFSH) have been used more recently. The efficacy of ovarian stimulation protocols may be enhanced using long gonadotropin hormone releasing hormone (GnRH) agonists or GnRH antagonists for cycle control. See, e.g., Devroey et al. *Fertility and Sterility* 97: 561-71 (2012).

Because patient responses to ovarian stimulation vary widely, treatments often are individualized. For example, individualization may be based on predicted ovarian response to gonadotropin stimulation, which forecasts poor, normal or high response. High ovarian responders usually are defined as women who produce high numbers of developing follicles following a standard protocol of controlled ovarian stimulation (COS). Although these patients are generally considered good candidates for ART, high ovarian response may be associated with lower implantation rates and higher miscarriage rates, and thus a decreased chance of successful outcome as compared with a normal ovarian response. These high responders also are at greater risk for OHSS and the complications associated therewith.

It has been hypothesized that ovarian stimulation may have a general negative impact on embryo quality, as assessed by morphological parameters and/or chromosomal analysis (e.g., euploidy vs. aneuploidy). See, e.g., Hamdine et al., "Ovarian Stimulation for IVF: Mild Approaches" in Human Fertility: Methods and Protocols, Methods in Molecular Biology, Vol. 1154, Springer Science+Business Media, New York (2014). Additionally, Haaf et al., *Fertility and Sterility* 91(3): 733-38 (2009), reported that a high oocyte yield is associated with an increased chromosome error rate. However, Fatemi et al., *Human Reproduction* 28(2) 442-52 (2013), reported that high ovarian response does not jeopardize ongoing pregnancy rates, but rather increases cumulative pregnancy rates.

Efforts to develop improved ART methods have involved exploring milder stimulation protocols. For example, Rubio et al., *Human Reproduction* 25(9): 2290-2010 (2010), reported that decreasing the gonadotrophin dose administered to high responders could improve fertilization rates and embryo quality, although the lower doses resulted in a decreased number of oocytes. Other efforts have considered whether the specific gonadotrophin used impacts the results. For example, Ziebe et al., *Human Reproduction* 22(9) 2404-13 (2007), reported that the use of HP-hMG versus rFSH could impact the morphology of embryos, and observed improved implantation, ongoing pregnancy and live birth rates among the top-quality embryos derived from stimulation with HP-hMG compared with rFSH. However, Ziebe's findings were based on a visual assessment of oocyte/embryo morphology on day three following retrieval, not based on chromosomal analysis, and morphology at day three is not correlated with aneuploidy. Along the same lines, La Marca et al., *Fertility and Sterility* O-169 (2012), reported that among predicted high responders (subjects having an AMH≥5.2 ng/ml) the group stimulated with rFSH group had significantly more oocytes retrieved, but a significantly lower live birth rate per cycle as compared to the group stimulated with HP-hMG.

There remains a need, therefore, for improved assisted reproductive technology methods, particularly for women at risk of a high response to controlled ovarian stimulation.

SUMMARY

In accordance with some embodiments, there are provided assisted reproductive technology methods useful for women at risk of a high response to controlled ovarian stimulation, comprising selecting a woman at risk of a high ovarian response to controlled ovarian stimulation having a serum anti-Müllerian hormone (AMH) level greater than or equal to 5.0±0.5 ng/ml, when measured using a Beckmann-Coulter Gen 2 assay or a comparable AMH level measured by a different method, and administering to the selected woman an amount of highly purified menotropin (HP-hMG) effective to stimulate follicle development. In accordance with some embodiments, the methods are for improving the quality of an embryo produced by in vitro fertilization after controlled ovarian stimulation in a woman at risk of a high ovarian response thereto. In accordance with other embodiments, the methods are for increasing the proportion of euploid blastocysts produced by in vitro fertilization after controlled ovarian stimulation in a woman at risk of a high ovarian response thereto. In accordance with other embodiments, the methods are for treating infertility in a woman at risk of a high ovarian response to controlled ovarian stimulation. In accordance with other embodiments, the methods are for effecting controlled ovarian stimulation in a woman at risk of a high ovarian response thereto. In accordance with other embodiments, the methods are for increasing ongoing pregnancy rates. In accordance with other embodiments, the methods are for increasing live birth rates. In accordance with other embodiments, the methods are for promoting the development of euploid blastocysts, such as for future blastocyst transfer, in a woman at risk of a high ovarian response to controlled ovarian stimulation.

In accordance with other embodiments, there are provided assisted reproductive technology methods useful for women at risk of a high response to controlled ovarian stimulation, comprising administering an amount of highly purified menotropin (HP-hMG) effective to stimulate follicle development to a woman selected as being at risk of a high ovarian response to controlled ovarian stimulation, wherein the selected woman has a serum anti-Müllerian hormone (AMH) level greater than or equal to 5.0±0.5 ng/ml, when measured using a Beckmann-Coulter Gen 2 assay or a comparable AMH level measured by a different method. In accordance with some embodiments, the methods are for improving the quality of an embryo produced by in vitro fertilization after controlled ovarian stimulation in a woman at risk of a high ovarian response thereto. In accordance with other embodiments, the methods are for increasing the proportion of euploid blastocysts produced by in vitro fertilization. In accordance with other embodiments, the methods are for treating infertility in a woman at risk of a high ovarian response to controlled ovarian stimulation. In accordance with other embodiments, the methods are for effecting controlled ovarian stimulation in a woman at risk of a high ovarian response thereto. In accordance with other embodiments, the methods are for increasing ongoing pregnancy rates. In accordance with other embodiments, the methods are for increasing live birth rates. In accordance with other embodiments, the methods are for promoting the development of euploid blastocysts, such as for future blastocyst transfer, in a woman at risk of a high ovarian response to controlled ovarian stimulation.

In specific embodiments of any of these methods, the woman may have an antral follicle count (AFC) of greater than or equal to 10, or greater than or equal to 15, in both ovaries combined, prior to stimulation.

In specific embodiments of any of these methods, the method may result in an increased proportion of euploid blastocysts, and/or an increased proportion/percentage of euploid blastocysts versus aneuploid blastocysts, and/or a reduced aneuploidy rate, and/or an increased ongoing pregnancy rate, and/or an increased live birth rate, each as compared to a comparable method using recombinant follicle-stimulating hormone (rFSH) as the gonadotropin. In further specific embodiments of any of these methods, the method may result in an increased proportion of euploid blastocysts, and/or an increased proportion/percentage of euploid blastocysts versus aneuploid blastocysts, and/or a reduced aneuploidy rate, and/or an increased ongoing pregnancy rate, and/or an increased live birth rate, each as compared to a comparable method using recombinant follicle-stimulating hormone (rFSH) as the gonadotropin.

In specific embodiments of any of these methods, the amount of HP-hMG administered may be from 100-300 IU per day for from about 1 to about 20 days, or from 100-200 IU per day for from about 1 to about 20 days.

In specific embodiments of any of these methods, the HP-hMG may be administered for at least 5 days.

In specific embodiments of any of these methods, the methods may further comprise administering a gonadotropin hormone releasing hormone (GnRH) agonist or a GnRH antagonist.

In specific embodiments of any of these methods, the methods may further comprise one or more of administering an amount of hCG effective to trigger ovulation, harvesting oocytes from the woman, and in vitro fertilization of harvested oocytes (optionally, by intra-cytoplasmic sperm injection (ICSI)).

In specific embodiments of any of these methods, the methods may further comprise assessing the chromosomal quality of blastocysts obtained from the woman after in vitro fertilization of oocytes harvested from the woman. In further specific embodiments, the methods may further comprise transfer of a blastocyst determined to be a euploid blastocyst. In specific embodiments, the transfer may be fresh transfer. In further specific embodiments, the methods may further comprise freezing a blastocyst determined to be a euploid blastocyst.

The foregoing general description and the detailed description are exemplary and explanatory and are intended to provide further explanation of the invention. For detailed understanding of the invention, reference is made to the following detailed description of specific embodiments, taken in conjunction with the accompanying figures. Other objects, advantages and novel features will be readily apparent to those skilled in the art from the following detailed description of the invention.

DETAILED DESCRIPTION

Figure 1:
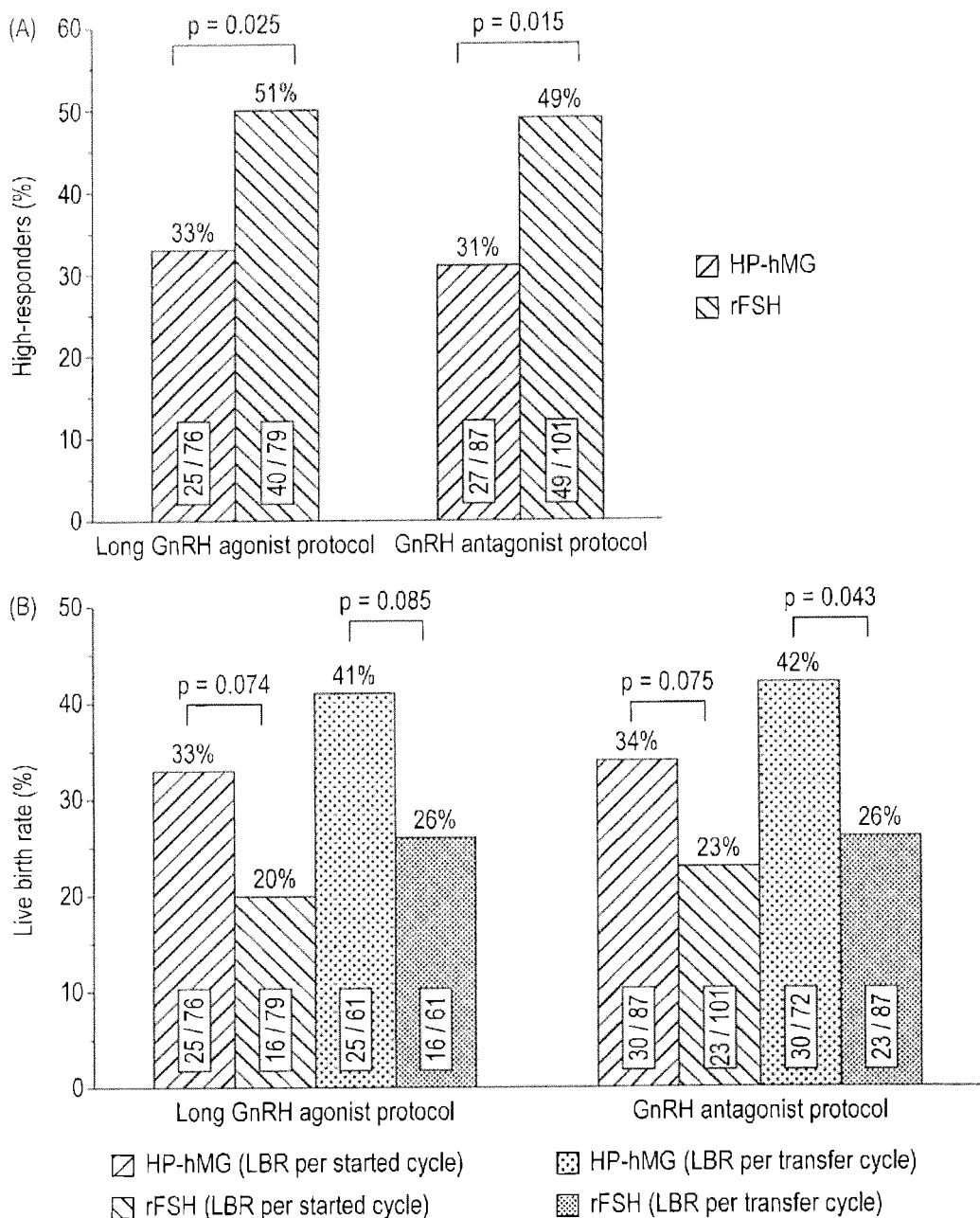
FIG. 1 shows (A) the occurrence of high ovarian response (≥15 oocytes retrieved) and (B) live birth rates (LBR) among women classified as potential high responders by a high initial anti-Müllerian hormone (AMH) level. Values within bars are n/total. p Values are based on the Chi-Square Test. The percentage of women with a high ovarian response is significantly lower for HP-hMG compared with rFSH in both the long agonist and the antagonist protocols.

Described herein are assisted reproductive technology methods, e.g., methods for treating infertility. In particular, described herein are controlled ovarian stimulation (COS) methods that may be particularly useful for women at risk of a high ovarian response to controlled ovarian stimulation. In some embodiments, the methods are useful for optimizing ovarian response to COS, improving embryo quality, increasing the proportion of euploid blastocysts produced by in vitro fertilization after controlled ovarian stimulation, decreasing the proportion of aneuploid blastocysts produced by in vitro fertilization after controlled ovarian stimulation, increasing ongoing pregnancy rates and/or increasing live birth rates.

The present invention is based on the unexpected finding by the inventors that the use of highly purified menotropin (HP-hMG) in potential high ovarian responders undergoing controlled ovarian stimulation (COS) may optimize ovarian response, improve embryo quality, increase the proportion of euploid blastocysts, decrease the proportion of aneuploid blastocysts, and improve ongoing pregnancy rates, and increases live birth rates.

Definitions

Technical and scientific terms used herein have the meanings commonly understood by one of ordinary skill in the art of assisted reproductive technology to which the present invention pertains, unless otherwise defined. Reference is made herein to various methodologies known to those of ordinary skill in the art. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

As used herein, the term "about" means that the number or range is not limited to the exact number or range set forth, but encompass ranges around the recited number or range as will be understood by persons of ordinary skill in the art depending on the context in which the number or range is used. Unless otherwise apparent from the context or convention in the art, "about" mean up to plus or minus 10% of the particular term.

As used herein, "optimizing ovarian response" refers to optimizing ovarian response to COS to achieve an optimal number of developing follicles, such as from 4-15 developing follicles, about 8-15 developing follicles, about 8-14 developing follicles, or about 11 developing follicles.

As used herein, "improving embryo quality" refers to increasing the proportion of euploid blastocysts (e.g., blastocysts having the correct number of chromosomes) and/or decreasing the proportion of aneuploid blastocysts (e.g., blastocysts having an incorrect number of chromosomes) produced in a single cycle of ART that involves COS followed by in vitro fertilization.

As used herein "ongoing pregnancy" refers to pregnancy with a viable fetus and detectable fetal heartbeat at 10-11 weeks gestation, e.g., at 8-9 weeks post blastocyst/embryo transfer.

As used herein "clinical pregnancy" refers to gestation and a detectable fetal heartbeat at 5-6 weeks gestation, e.g., at 3-4 weeks post blastocyst/embryo transfer.

As used herein, "woman" refers to an adult female human. In some embodiments, a woman treated in accordance with the methods described herein is 35 years old or younger, or is 34 years old or younger. In some embodiments, a woman treated in accordance with the methods described herein is 21-38 years old, or 21-37, or 21-36, or 21-34, or 21-32, or 21-30 years old. In some embodiments, a woman treated in accordance with the methods described herein has a BMI of 38 kg/m$^2$ or less, 36 kg/m$^2$ or less, 34 kg/m$^2$ or less, 32 kg/m$^2$ or less, 30 kg/m$^2$ or less, or 28 kg/m$^2$ or less, such as BMI of 18-38, 18-36, 18-34, 18-32, 18-30, or 18-28 kg/m$^2$. In some embodiments, a woman treated in accordance with the methods described herein has a BMI of 18-25 kg/m$^2$, 18-26 kg/m$^2$, 18-29 kg/m$^2$, 18-30 kg/m$^2$, 18-32 kg/m$^2$, 18-34 kg/m$^2$, 18-36 kg/m$^2$, or 18-38 kg/m$^2$. In some embodiments, a woman treated in accordance with the methods described herein is an ovulatory woman, i.e., is not anovulatory. In some embodiments, a woman treated in accordance with the methods described herein is an ovulatory woman with menstrual cycles of no greater than 45 days.

As used herein, subjects classified as being "at risk of a high ovarian response to controlled ovarian stimulation" refers to women who are likely to develop high numbers of follicles or oocytes following a standard protocol of controlled ovarian stimulation (COS), such as women with a greater than average likelihood of producing 15 or more oocytes. Women may be identified as being at risk if they have generated 15 or more oocytes in a previous ART cycle, e.g., in a previous COS treatment. Additionally or alternatively, women may be identified as being at risk if they are considered to be at risk of developing OHSS. Additionally or alternatively, women may be identified as being at risk if they have a serum level of anti-Müllerian hormone (AMH) of greater than or equal to about 5.0 ng/ml (such as greater than or equal to about 5.0 ng/ml) when assessed as described herein below (or an equivalent level when assessed by a different method). Additionally or alternatively, women may be identified as being at risk if they have an antral follicle count (AFC) of greater than or equal to 15, greater than or equal to 18, or greater than or equal to 20, in both ovaries combined, prior to stimulation.

The term "menotropin" as used herein includes human menopausal gonadotropin or hMG. The term "highly purified menotropin" as used herein includes HP-hMG available under the trademark MENOPUR® from Ferring B. V., that contains both follicle stimulating hormone (FSH) and human chorionic gonadotrophin (hCG)-driven luteinizing hormone (LH)-activity.

The term "GnRH agonist" as used herein includes gonadotropin-releasing hormone (GnRH) agonists such as buserelin (e.g., Suprecur®), leuprorelin (e.g., Lupron®), nafarelin (e.g., Synarel®), and triptorelin (e.g., Trelstar®).

The term "GnRH antagonist" as used herein includes gonadotropin-releasing hormone (GnRH) antagonists, such as ganirelix acetate (e.g., Orgalutran®) and cetrorelix acetate (e.g., Cetrotide®), which block the action of GnRH by competitive blocking of the GnRH receptors on pituitary gonadotropes, and thus prevent gonadotropin production and eggs premature release.

As used herein, the phrase "effective amount" refers to the dosage that provides the specific pharmacological effect for which the drug is administered in a subject in need of such treatment. It is emphasized that a therapeutically effective amount will not always be effective in treating the conditions described herein, even though such dosage is deemed to be a therapeutically effective amount by those of skill in the art. For convenience only, exemplary dosages and therapeutically effective amounts are provided below with reference to adult female human subjects. Those skilled in the art can adjust such amounts in accordance with standard practices as needed to treat a specific subject and/or condition/disease.

As noted above, the present invention provides reproductive technology methods that involve using highly purified menotropin (HP-hMG) in women at risk of a high ovarian response to COS and undergoing COS. As also noted above, for the purposes of the methods disclosed herein, women may be identified as being at risk of a high ovarian response to COS if they have a serum level of anti-Müllerian hormone (AMH) of greater than or equal to about 5.0 ng/ml, such as greater than or equal to 5.0±0.5 ng/ml, such as greater than or equal to 5.2±0.5 ng/ml, such as greater than or equal to about 5.0±0.5 ng/ml, such as greater than or equal to about 5.2±0.5 ng/ml, when measured using a Beckmann-Coulter Gen 2 assay as described in Arce et al., *Fertility and Sterility* 99: 1644-53 (2013), or an equivalent AMH level assessed by a different method (± its coefficient of variability). Serum levels of AMH are a surrogate marker for functional ovarian follicle reserve, and a positive correlation between serum levels of AMH and ovarian response (e.g., oocyte yield) have been reported. Id. However, according to Arce et al., AMH levels have not been correlated with embryo quality. Id.

Additionally or alternatively, as also noted above, for the purposes of the methods disclosed herein, women may be identified as being at risk of a high ovarian response to COS if they have an antral follicle count (AFC) of greater than or equal to 15, greater than or equal to 18, or greater than or equal to 20, in both ovaries combined, prior to stimulation. Antral follicles are small follicles (about 2-8 mm in diameter) that can be visualized and measured via transvaginal ultrasound. Antral follicles are another marker for ovarian reserve, and AFC has been used (along with other markers) to predict ovarian response to COS, e.g., to predict whether a given subject will be a low, normal, or high responder. However, AFC has not been correlated with embryo quality.

Assisted Reproductive Technology Methods

The methods described herein are useful in any reproductive technology methods that involve controlled ovarian stimulation (COS), such as for in vitro fertilization, including intra-cytoplasmic sperm injection (ICSI), including methods involving fresh transfer of fertilized eggs (e.g., blastocysts/embryos) and methods that involving freezing fertilized eggs (e.g., blastocysts/embryos) for later implantation.

In specific embodiments, the subject undergoing COS is at risk of a high ovarian response to COS. In specific embodiments, the subject is identified by having a serum level of AMH of greater than or equal to about 5.0 ng/ml, such as greater than or equal to 5.0±0.5 ng/ml, such as greater than or equal to about 5.0±0.5 ng/ml ng/ml, such as greater than or equal to 5.2±0.5 ng/ml, such as greater than or equal to about 5.2±0.5 ng/ml ng/ml, when measured using a Beckmann-Coulter Gen 2 assay as described in Arce et al., *Fertility and Sterility* 99: 1644-53 (2013), or an equivalent AMH level assessed by a different method (± its coefficient of variability).

In some embodiments, the subject is additionally or alternatively identified by having an AFC of greater than or equal to 15, greater than or equal to 18, or greater than or equal to 20, in both ovaries combined, prior to stimulation. In some embodiments, the subject is excluded from treatment by the methods described herein if the subject has an AFC of less than 8, or less than 10, in both ovaries combined, prior to stimulation. In some embodiments, subjects treated by the methods described herein have an AFC of at least 10 (≥10) in both ovaries combined prior to stimulation.

The subject may be additionally or alternatively identified as being at risk if they have generated 15 or more oocytes in a previous ART cycle, e.g., in a previous COS treatment, and/or if they are considered to be at risk of developing OHSS.

In specific embodiments, the methods include administering HP-hMG to the subject in an amount effective to stimulate follicle development. In some embodiments, HP-hMG is administered at a dose of from about 75 IU or 100 IU to about 300 IU/day, or from about 100 to about 200 IU/day, for from about 1 to about 20 days, such as for at least 5 days. Pharmaceutical compositions comprising HP-hMG are available commercially, such as the MENOPUR® product sold by Ferring B. V., which is formulated for subcutaneous injection. Typically, a starting dose is 150 IU/day for the first 5 days, which may be adjusted thereafter (e.g., on day 6 onward) based on the subject's ovarian (follicular) response, which may be assessed, for example, by transvaginal ultrasound (TVUS). For example, once the lead follicle reaches >12 mm in diameter, the dose can be adjusted by 75 IU per adjustment. Typically, the dose is adjusted up or down when both the serum estradiol level and the number of follicles>12 mm are either too low or too high on the 6 day of stimulation. HP-hMG is administered daily until the desired level of follicle production is reached. For example, HP-hMG may be administered until three follicles have developed with a diameter of >17 mm, as may be determined by TVUS. Typically, the maximum HP-hMG dosing period is 20 days.

In some embodiments, the methods include the administration of a GnRH antagonist during a portion of the period of HP-hMG administration. For example, a GnRH antagonist may be administered once the lead follicle reaches 14 mm in diameter, and continued through the remainder of the period of HP-hMG administration. When the GnRH antagonist is ganirelix acetate (such as Orgalutran®), a typical dose is 0.25 mg/day administered subcutaneously.

In other embodiments, the methods include the administration of a GnRH agonist prior to ovarian stimulation, such as the administration of triptorelin (typically at 0.1 mg/day subcutaneously) or leuprorelin (e.g., Lupron®).

Once the desired level of follicle production is reached, ovulation can be stimulated by methods known in the art, such as by a bolus injection of human chorionic gonadotropin (hCG). A typical dose of recombinant hCG (such as Ovitrelle®) is 250 μg (6,500 IU of hCG activity), usually administered by a single subcutaneous injection. Then, oocytes are retrieved and fertilized by methods known in the art, such as ICSI.

For fresh transfer methods, one or more blastocysts are selected for transfer a few days after fertilization (e.g. after 5 days). Remaining blastocysts can be frozen by methods known in the art for future transfer (including vitrification). In specific embodiments, the methods described herein are used in a single blastocyst transfer protocol, wherein a single blastocyst is selected for fresh transfer. In accordance with those embodiments, remaining blastocysts can be frozen by methods known in the art for future transfer.

For "freeze all" methods, selected blastocysts are frozen by methods known in the art for future transfer.

In specific embodiments, blastocyst selection is guided by morphological analysis. For example, morphological blastocyst quality can be assessed by determining blastocyst expansion and hatching status, inner cell mass grading and trophectoderm grading according to the Gardner blastocyst grading system. See, e.g., Van den Abbeel et al., *Reproductive Biomed. OnLine* 27: 353-61 (2013). For example, blastocysts with blastocyst expansion and hatching status 4, 5 or 6, inner cell mass grading A, and trophectoderm grading A or B may be deemed of "excellent" quality, while blastocysts with blastocyst expansion and hatching status 3, 4, 5 or 6, inner cell mass grading A or B, and trophectoderm grading A or B may be deemed of "good" quality.

Additionally or alternatively, blastocyst quality is assessed by chromosomal analysis, including genetic screening (e.g., preimplantation genetic screening, or PGS) to detect aneuploidy. In some embodiments, chromosomal analysis includes comprehensive chromosomal screening (CCS) as described, for example, in Forman et al., *Fertility and Sterility* 100: 718-24 (2013). As reported in this paper, CCS can be conducted prior to fresh transfer or prior to blastocyst freezing for future transfer.

In some embodiments, luteal phase support is provided by the administration of progesterone, such as vaginal progesterone inserts, from the day after oocyte retrieval to 10-15 days after blastocyst/embryo transfer, and/or from the day of blastocyst/embryo transfer to the confirmation of ongoing pregnancy, in accordance with protocols known in the art.

In some embodiments, clinical pregnancy is confirmed by TVUS at 5-6 weeks gestation (e.g., 3-4 weeks after blastocyst/embryo transfer). In some embodiments, ongoing pregnancy is confirmed by TVUS at 10-11 weeks gestation (e.g., 8-9 weeks after blastocyst/embryo transfer).

In some embodiments, the subject is followed to assess pregnancy outcome (e.g. live birth) and/or neonatal health.

As set forth above, the methods described herein are useful for improving embryo quality, increasing the proportion of euploid blastocysts, decreasing the proportion of aneuploid blastocysts, increasing ongoing pregnancy rates and/or increasing live birth rates, as compared to comparable methods using recombinant follicle stimulating hormone (rFSH) as the gonadotropin. In particular, the methods described herein may result in an increased proportion of euploid blastocysts (e.g., a decreased proportion of aneuploidy blastocysts), as compared to comparable methods using rFSH as the gonadotropin. The methods described herein also may result in increased ongoing pregnancy rates and/or increased live birth rates, as compared to comparable methods using rFSH as the gonadotropin, such as an 8% or 10% or greater increase in ongoing pregnancy rates and/or increased live birth rates. In some embodiments, the methods result in fewer eggs but a higher proportion of euploid blastocysts as compared to comparable methods using rFSH as the gonadotropin.

The following exemplary methods are encompassed by the foregoing disclosure:

A method for improving the quality of an embryo produced by in vitro fertilization after controlled ovarian stimulation in a woman at risk of a high ovarian response thereto, comprising selecting a woman at risk of a high ovarian response to controlled ovarian stimulation having a serum anti-Müllerian hormone (AMH) level greater than or equal to 5.0±0.5 ng/ml, when measured using a Beckmann-Coulter Gen 2 assay or a comparable AMH level measured by a different method; and administering to the selected woman an amount of highly purified menotropin (HP-hMG) effective to stimulate follicle development.

A method for improving the quality of an embryo produced by in vitro fertilization after controlled ovarian stimulation in a woman at risk of a high ovarian response thereto, comprising administering an amount of highly purified menotropin (HP-hMG) effective to stimulate follicle development to a woman selected as being at risk of a high ovarian response to controlled ovarian stimulation, wherein the selected woman has a serum anti-Müllerian hormone (AMH) level greater than or equal to 5.0±0.5 ng/ml, when measured using a Beckmann-Coulter Gen 2 assay or a comparable AMH level measured by a different method.

A method for increasing the proportion of euploid blastocysts produced by in vitro fertilization after controlled ovarian stimulation in a woman at risk of a high ovarian response thereto, comprising selecting a woman at risk of a high ovarian response to controlled ovarian stimulation having a serum anti-Müllerian hormone (AMH) level greater than or equal to 5.0±0.5 ng/ml when measured using a Beckmann-Coulter Gen 2 assay or a comparable AMH level measured by a different method; and administering to the selected woman an amount of highly purified menotropin (HP-hMG) effective to stimulate follicle development.

A method for increasing the proportion of euploid blastocysts produced by in vitro fertilization after controlled ovarian stimulation in a woman at risk of a high ovarian response thereto, comprising administering an amount of highly purified menotropin (HP-hMG) effective to stimulate follicle development to a woman selected as being at risk of a high response to controlled ovarian stimulation, wherein the selected woman has a serum anti-Müllerian hormone (AMH) level greater than or equal to 5.0±0.5 ng/ml when measured using a Beckmann-Coulter Gen 2 assay or a comparable AMH level measured by a different method.

A method for treating infertility in a woman at risk of a high ovarian response to controlled ovarian stimulation, comprising selecting a woman at risk of a high ovarian response to controlled ovarian stimulation having (i) a serum anti-Müllerian hormone (AMH) level greater than or equal to 5.0±0.5 ng/ml when measured using a Beckmann-Coulter Gen 2 assay or a comparable AMH level measured by a different method; and administering to the selected woman an amount of highly purified menotropin (HP-hMG) effective to stimulate follicle development.

A method for treating infertility in a woman at risk of a high ovarian response to controlled ovarian stimulation, comprising administering an amount of highly purified menotropin (HP-hMG) effective to stimulate follicle development to a woman selected as being at risk of a high ovarian response to controlled ovarian stimulation, wherein the selected woman has a serum anti-Müllerian hormone (AMH) level greater than or equal to 5.0±0.5 ng/ml when measured using a Beckmann-Coulter Gen 2 assay or a comparable AMH level measured by a different method.

A method for effecting controlled ovarian stimulation in a woman at risk of a high ovarian response thereto, comprising selecting a woman at risk of a high ovarian response to controlled ovarian stimulation having a serum anti-Müllerian hormone (AMH) level greater than or equal to 5.0±0.5 ng/ml when measured using a Beckmann-Coulter Gen 2 assay or a comparable AMH level measured by a different method; and administering to the selected woman an amount of highly purified menotropin (HP-hMG) effective to stimulate follicle development.

A method for effecting controlled ovarian stimulation in a woman at risk of a high ovarian response thereto, comprising administering an amount of highly purified menotropin (HP-hMG) effective to stimulate follicle development to a woman selected as being at risk of a high ovarian response to controlled ovarian stimulation, wherein the selected woman has a serum anti-Müllerian hormone (AMH) level greater than or equal to 5.0±0.5 ng/ml when measured using a Beckmann-Coulter Gen 2 assay or a comparable AMH level measured by a different method.

A method for increasing ongoing pregnancy rates in a woman at risk of a high ovarian response to controlled ovarian stimulation, comprising selecting a woman at risk of a high ovarian response to controlled ovarian stimulation having a serum anti-Müllerian hormone (AMH) level greater than or equal to 5.0±0.5 ng/ml when measured using a Beckmann-Coulter Gen 2 assay or a comparable AMH level measured by a different method; and administering to the selected woman an amount of highly purified menotropin (HP-hMG) effective to stimulate follicle development.

A method for increasing ongoing pregnancy rates in a woman at risk of a high ovarian response to controlled ovarian stimulation, comprising administering an amount of highly purified menotropin (HP-hMG) effective to stimulate follicle development to a woman selected as being at risk of a high ovarian response to controlled ovarian stimulation, wherein the selected woman has a serum anti-Müllerian hormone (AMH) level greater than or equal to 5.0±0.5 ng/ml when measured using a Beckmann-Coulter Gen 2 assay or a comparable AMH level measured by a different method.

A method for increasing live birth rates in a woman at risk of a high ovarian response to controlled ovarian stimulation, comprising selecting a woman at risk of a high ovarian response to controlled ovarian stimulation having a serum anti-Müllerian hormone (AMH) level greater than or equal to 5.0±0.5 ng/ml when measured using a Beckmann-Coulter Gen 2 assay or a comparable AMH level measured by a different method; and administering to the selected woman an amount of highly purified menotropin (HP-hMG) effective to stimulate follicle development.

A method for increasing live birth rates in a woman at risk of a high ovarian response to controlled ovarian stimulation, comprising administering an amount of highly purified menotropin (HP-hMG) effective to stimulate follicle development to a woman selected as being at risk of a high ovarian response to controlled ovarian stimulation, wherein the selected woman has a serum anti-Müllerian hormone (AMH) level greater than or equal to 5.0±0.5 ng/ml when measured using a Beckmann-Coulter Gen 2 assay or a comparable AMH level measured by a different method.

A method for promoting the development of euploid blastocysts in a woman at risk of a high ovarian response to controlled ovarian stimulation, comprising selecting a woman at risk of a high ovarian response to controlled ovarian stimulation having a serum anti-Müllerian hormone (AMH) level greater than or equal to 5.0±0.5 ng/ml when measured using a Beckmann-Coulter Gen 2 assay or a comparable AMH level measured by a different method; and administering to the selected woman an amount of highly purified menotropin (HP-hMG) effective to stimulate follicle development.

A method for promoting the development of euploid blastocysts in a woman at risk of a high ovarian response to controlled ovarian stimulation, comprising administering an amount of highly purified menotropin (HP-hMG) effective to stimulate follicle development to a woman selected as being at risk of a high ovarian response to controlled ovarian stimulation, wherein the selected woman has a serum anti-Müllerian hormone (AMH) level greater than or equal to 5.0±0.5 ng/ml when measured using a Beckmann-Coulter Gen 2 assay or a comparable AMH level measured by a different method.

In any of these methods, the woman may have an antral follicle count (AFC) of greater than or equal to 10 in both ovaries combined, prior to stimulation.

In any of these methods, the woman may have an antral follicle count (AFC) of greater than or equal to 15 in both ovaries combined, prior to stimulation.

Any of these methods may result in an increased proportion of euploid blastocysts as compared to a comparable method using recombinant follicle-stimulating hormone (rFSH) as the gonadotropin, and/or an increased ongoing pregnancy rate, and/or an increased live birth rate.

In any of these methods, the amount of HP-hMG administered may be from 100-300 IU per day for from about 1 to about 20 days, or from 100-200 IU per day for from about 1 to about 20 days.

In any of these methods, the HP-hMG may be administered for at least 5 days.

Any of these methods may further comprise administering a gonadotropin hormone releasing hormone (GnRH) agonist, and/or a GnRH antagonist.

Any of these methods may further comprise administering an amount of hCG effective to trigger ovulation, harvesting oocytes from the woman, in vitro fertilization of harvested oocytes (such as intra-cytoplasmic sperm injection (ICSI)), assessing the chromosomal quality of blastocysts obtained from the woman after in vitro fertilization of oocytes harvested from the woman, blastocyst transfer of a blastocyst determined to be a euploid blastocyst (such as fresh transfer), and/or freezing a blastocyst determined to be a euploid blastocyst.

Further aspects of the methods described herein are illustrated in the following examples, which are not limiting in any respect.

EXAMPLES

Example 1—Retrospective Analysis

A retrospective analysis was undertaken of data collected in two randomized controlled clinical trials comparing treatment outcome in patients undergoing stimulation with HP-hMG or recombinant FSH following a long GnRH agonist protocol (Anckaert et al., *Human Reproduction* 27: 1829-39 (2012)) or a GnRH antagonist protocol (Arce el al., *Fertility and Sterility,* 99: 1644-53 (2013).

1. Study Populations

The main inclusion criteria for the long agonist trial were women aged 21-37 years with major indications for IVF (such as tubal factor infertility, unexplained infertility or mild male factor infertility), FSH levels within normal limits (1-12 IU/L), BMI of 18-29, and regular menstrual cycles of 21-35 days which were presumed to be ovulatory. The main inclusion criteria for the antagonist trial were women aged 21-34 years with a primary infertility diagnosis of unexplained infertility or mild male factor infertility, FSH levels of 1-12 IU/L, BMI of 18-25, and regular menstrual cycles of 24-35 days, 2. Study Protocols In the long agonist protocol, down-regulation was performed using triptorelin (0.1 mg/day) (Decapeptyl®, Ferring Pharmaceuticals A/S) initiated 5-7 days before the estimated start of next menses and continued until the end of gonadotropin administration. Gonadotropin (HP-hMG or rFSH) was administered at 225 IU/day for the first 5 days, and then adjusted according to ovarian response.

In the antagonist protocol, gonadotropin (HP-hMG or rFSH) was administered at 150 IU/day for the first 5 days, and then adjusted according to ovarian response from day 6. On day 6 GnRH antagonist (ganirelix, Orgalutran, MSD) was initiated at 0.25 mg/day and continued throughout gonadotropin-treatment.

In both protocols, 250 μg hCG (Choriogonadotropin alpha, Ovitrelle, Merck Serono) was administered when three follicles of ≥17 mm diameter were observed, and oocyte retrieval took place 36±2 hours later.

Luteal support was provided by vaginal administration of progesterone

In the long agonist protocol, 1 or 2 embryos were transferred on day 3. In the antagonist protocol, 1 blastocyst was transferred on day 5.

Live birth was defined as delivery of (at least) one live-born neonate.

3. Serum Assays

AMH was analyzed by enzyme-linked immunosorbent assay (long agonist trial: Immunotech Beckman Coulter AMH ELISA; antagonist trial: Beckman Coulter Gen 2 ELISA; 1 ng/ml=7.14 pmol/L). The AMH assays had a sensitivity of 0.35 and 0.08 ng/ml and total imprecision (% coefficient of variation) of <9.5 and <7.7 in Immunotech Beckman Coulter and Beckman Coulter Gen 2, respectively. FSH, estradiol and progesterone were analyzed by electro-chemiluminescence immunoassay (Roche-Diagnostics ECLIA).

4. Statistical Analysis

In total, the two trials comprised 1372 women. In the retrospective analysis, women were classified as potential high-responders if initial AMH was in the uppermost quartile ($75^{th}$ percentile) of the observed AMH distribution. In both protocols, the $75^{th}$ percentile was identical (5.2 ng/ml=37.4 pmol/l). In the retrospective analysis, one hundred fifty-five women treated in the long GnRH agonist protocol (76 and 79 in the HP-hMG and rFSH groups, respectively) and 188 women in the GnRH antagonist protocol (87 and 101 in the HP-hMG and rFSH groups, respectively) were classified as potential high-responders.

In each protocol, baseline characteristics, end-of-stimulation data, ovarian response and embryo data were compared between the women grouped according to their AMH value on stimulation day 1 (>75th versus≥75th percentile). Similar analyses were performed for the potential high-responders comparing gonadotropin treatments (HP-hMG versus rFSH) within each protocol. Continuous and categorical data were compared using the Wilcoxon test and the Chi-Square or Fisher's exact test, respectively. For the potential high-responders, risk of high response (≥15 oocytes retrieved) and chance of live birth were compared between treatments using the Chi-square test. The observed differences in live birth rates between gonadotropin-treatment groups were further analyzed in the pooled population of potential high-responders from both protocols to determine if they could be attributed to baseline characteristics or end-of-stimulation variables. For each variable, a logistic regression model was fitted including treatment group and the variable in question in the linear predictor. Only fresh treatment cycles were included in the present dataset.

5. Results

High AMH Category Versus Non-High AMH Category

In both the long agonist protocol and the antagonist protocol, the women in the high AMH category were characterized by younger age, longer menstrual cycle length, higher AFC, lower FSH and larger ovarian volume at start of stimulation than women in the non-high AMH category (p≤0.003 for each variable). These features are shown in Table 1.

TABLE 1

Demographics and baseline, end-of-stimulation, oocyte and embryo data of the women grouped by the AMH concentration at start of stimulation (quartiles 1-3 versus quartile 4).

| | Long GnRH agonist protocol | | | GnRH antagonist protocol | | |
|---|---|---|---|---|---|---|
| Variable | AMH Q1-Q3 ≤ 75th (≤5.2 ng/ml) (n = 468) | AMH Q4 > 75th (>5.2 ng/ml) (n = 155) | p Value* | AMH Q1-Q3 ≤ 75th (≤5.2 ng/ml) (n = 561) | AMH Q4 > 75th (>5.2 ng/ml) (n = 188) | p Value* |
| Clinical characteristics | | | | | | |
| Age (years) | 31 (29, 34) | 30 (28, 32) | <0.001 | 31 (29, 33) | 30 (28, 32) | <0.001 |
| BMI (kg/m$^2$) | 21.9 (20.3, 24.0) | 21.3 (20.1, 23.5) | 0.113 | 21.9 (20.3, 23.8) | 21.8 (20.5, 23.5) | 0.868 |
| Cycle length (days) | 28 (28, 29) | 29 (28, 30) | <0.001 | 28 (28, 29) | 29 (28, 30) | <0.001 |
| First treatment cycle, n (%) | 327 (70%) | 104 (67%) | 0.517 | 427 (76%) | 134 (71%) | 0.186 |
| Day 1 (before stimulation) | | | | | | |
| Ovarian volume (ml) | 8.5 (6.0, 11.8) | 10.4 (7.7, 14.3) | <0.001 | 10.6 (8.0, 14.2) | 13.2 (9.6, 16.8) | <0.001 |
| AFC (n) | 10 (7, 14) | 11 (8, 18) | <0.001 | 14 (11, 17) | 18 (15, 22) | <0.001 |
| AMH (ng/ml) | 3.0 (2.1, 4.0) | 7.0 (5.8, 8.5) | <0.001 | 2.4 (1.4, 3.6) | 6.9 (6.0, 8.7) | <0.001 |
| FSH (IU/l) | 3.8 (3.0, 4.9) | 3.4 (2.7, 4.4) | 0.003 | 7.2 (6.2, 8.5) | 6.5 (5.7, 7.6) | <0.001 |
| End-of-stimulation | | | | | | |
| Estradiol (nmol/l) | 5.5 (4.0, 7.3) | 8.5 (6.2, 13.0) | <0.001 | 5.7 (4.1, 8.2) | 8.7 (6.3, 13.3) | <0.001 |
| Progesterone (nmol/l) | 2.6 (2.0, 3.4) | 3.2 (2.4, 3.9) | <0.001 | 2.5 (1.9, 3.2) | 2.9 (2.1, 3.8) | <0.001 |
| Progesterone/estradiol ratio | 0.46 (0.35, 0.63) | 0.36 (0.24, 0.49) | <0.001 | 0.42 (0.30, 0.60) | 0.32 (0.21, 0.44) | <0.001 |
| Follicles ≥12 mm (n) | 10 (8, 13) | 15 (12, 19) | <0.001 | 10 (7, 13) | 15 (11, 18) | <0.001 |
| Endometrial thickness (mm) | 11 (9, 12) | 11 (10, 12) | 0.079 | 10 (9, 12) | 11 (10, 12) | 0.039 |
| Endometrial echogenicity pattern (hypo, iso, hyper) (%) | 39, 49, 13 | 34, 51, 15 | 0.544 | 40, 51, 9 | 36, 54, 10 | 0.668 |
| Cycle cancellation for ovarian hyper-response, n (%) | 2 (<1%) | 7 (5%) | 0.001 | 1 (<1%) | 1 (<1%) | 0.439 |
| Early OHSS (moderate/severe), n (%) | 1 (<1%) | 7 (5%) | <0.001 | 4 (<1%) | 8 (4%) | 0.003 |
| Intervention for ovarian hyper-response, n (%) | 2 (<1%) | 11 (7%) | <0.001 | 16 (3%) | 19 (10%) | <0.001 |
| Oocyte retrieval | | | | | | |
| Women with oocyte retrieval, n (%) | 446 (95%) | 145 (94%) | 0.392 | 537 (96%) | 185 (98%) | 0.088 |
| Oocytes retrieved (n) | 9 (6, 12) | 14 (10, 18) | <0.001 | 8 (5, 11) | 12 (9, 17) | <0.001 |
| Women with ≥15 oocytes retrieved, n (%) | 76 (16%) | 65 (42%) | <0.001 | 63 (11%) | 76 (40%) | <0.001 |
| Fertilization and embryo data | | | | | | |
| Fertilisation rate (%) | 60 (33, 75) | 52 (29, 70) | 0.091 | 60 (43, 75) | 58 (42, 71) | 0.193 |
| Embryos, day 3 (n) | 2 (1, 5) | 3 (2, 6) | 0.029 | | | |
| Women with top-quality embryo(s), day 3, n (%)† | 199 (45%) | 73 (50%) | 0.229 | | | |
| Blastocysts, day 5 (n) | | | | 2 (1, 4) | 3 (1, 6) | <0.001 |
| Women with good-quality blastocyst(s), day 5, n (%)‡ | | | | 266 (50%) | 106 (57%) | 0.068 |
| Women with transfer, n (%)¶ | 397 (89%) | 122 (84%) | 0.119 | 462 (86%) | 159 (86%) | 0.976 |

Values are median (IQR) unless otherwise indicated.
*Wilcoxon test (continuous data); Chi-Square test or Fisher's exact test (categorial data).
†Top-quality embryos were defined as 4-5 cells on day 2, ≥7 cells on day 3, equally-sized blastomeres and ≤20% fragmentation on day 3 and no multinucleation.
‡Good-quality blastocysts were defined as blastocysts with expansion and hatching score ≥4 and with inner cell mass and trophectoderm grades of A or B, using the definitions described by Gardner & Schoolcraft, "In-vitro culture of human blastocysts," In TOWARDS REPRODUCTIVE CERTAINTY: FERTILITY AND GENETICS BEYOND 1998, Jansen & Mortimer, eds. (The Parthenon Publishing Group, New York 1999), pg. 378-88.
¶Among women with oocytes retrieved.

The retrospective analysis revealed that, independent of the protocol used, women with high AMH exhibited significantly (p<0.001 for each variable) higher serum levels of estradiol and progesterone as well as increased number of growing follicles≥12 mm at end of stimulation. Further, the women with high AMH had significantly (p≤0.003 for each variable) more oocytes retrieved, increased occurrence of high response, higher frequency of early OHSS and interventions for hyper-response. In the long agonist protocol, cycle cancellation due to ovarian hyper-response occurred more frequently among women in the high AMH category (p=0.001). At end of stimulation, no clinically relevant differences were noted in endometrial thickness or echogenicity patterns between the two AMH categories. Significantly more embryos on day 3 (long agonist protocol: p=0.029) or blastocysts on day 5 (antagonist protocol: p<0.001) were available in women with high AMH, but the proportion of women with top-quality embryo(s) or good-quality blastocyst(s) were similar in the two AMH categories.

6. HP-hMG Versus rFSH Stimulation in High AMH Category

Within each protocol, there were no clinically relevant differences between the two gonadotropin-treatment groups in the high AMH category regarding demographics, fertility history and markers of ovarian reserve, as shown in Table 2 below. BMI was significantly lower in rFSH-treated women, but was not believed to be of clinical relevance. (However, it is possible that a higher BMI could blunt ovarian response.) At the end of stimulation, higher estradiol levels (p=0.012) and lower progesterone levels (p<0.001) were observed with HP-hMG in the antagonist and long agonist protocol, respectively.

TABLE 2

Comparison of baseline, end-of-stimulation, oocyte and embryo characteristics between HP-hMG- and rFSH-treated women with potential for being high-responders by a high AMH at start of stimulation.

| Variable | Long GnRH agonist protocol AMH Q4: >75th (>5.2 ng/ml) | | | GnRH antagonist protocol AMH Q4: >75th (>5.2 ng/ml | | |
|---|---|---|---|---|---|---|
| | HP-hMG (n = 76) | rFSH (n = 79) | p Value * | HP-hMG (n = 87) | rFSH (n = 101) | p Value * |
| Clinical characteristics | | | | | | |
| Age (years) | 30 (28, 32) | 30 (28, 32) | 0.743 | 30 (28, 33) | 30 (28, 31) | 0.039 |
| BMI (kg/m$^2$) | 22.5 (20.7, 23.8) | 20.8 (19.8, 22.8) | 0.002 | 22.1 (21.0, 23.9) | 21.6 (20.1, 23.0) | 0.022 |
| Cycle length (days) | 29 (28, 30) | 29 (28, 30) | 0.682 | 29 (28, 30) | 29 (28, 31) | 0.382 |
| First treatment cycle, n (%) | 52 (68%) | 52 (66%) | 0.731 | 57 (66%) | 77 (76%) | 0.105 |
| Day 1 (before start of stimulation) | | | | | | |
| Ovarian volume (ml) | 10.3 (7.9, 13.9) | 10.5 (7.7, 14.8) | 0.807 | 13.4 (9.1, 17.0) | 13.0 (9.9, 16.7) | 0.885 |
| AFC (n) | 12 (8, 20) | 11 (8, 16) | 0.486 | 18 (15, 22) | 18 (15, 22) | 0.934 |
| AMH (ng/ml) | 7.0 (5.9, 8.5) | 7.0 (5.7, 8.4) | 0.912 | 7.1 (6.2, 8.7) | 6.8 (6.0, 8.3) | 0.347 |
| FSH (IU/1) | 3.2 (2.6, 4.4) | 3.6 (2.8, 4.4) | 0.257 | 6.7 (5.6, 7.7) | 6.4 (5.7, 7.5) | 0.251 |
| End-of-stimulation | | | | | | |
| Estradiol (nmol/1) | 8.7 (6.4, 13.0) | 8.4 (6.1, 12.8) | 0.736 | 9.7 (6.8, 14.8) | 7.8 (5.5, 12.4) | 0.012 |
| Progesterone (nmol/1) | 2.7 (1.9, 3.6) | 3.6 (2.8, 4.5) | <0.001 | 2.8 (2.1, 3.9) | 3.0 (2.1, 3.8) | 0.857 |
| Progesterone/estradiol ratio | 0.31 (0.21, 0.42) | 0.43 (0.30, 0.52) | <0.001 | 0.26 (0.20, 0.41) | 0.34 (0.24, 0.47) | 0.011 |
| Follicles ≥12 mm (n) | 15 (12, 18) | 16 (13, 19) | 0.274 | 14 (11, 18) | 16 (12, 19) | 0.064 |
| Endometrial thickness (mm) | 11 (10, 12) | 11 (10, 12) | 0.522 | 11 (10, 12) | 11 (10, 12) | 0.478 |
| Endometrial echogenicity pattern (hypo, iso, hyper) (%) | 44, 43, 13 | 24, 60, 17 | 0.033 | 31, 58, 11 | 41, 50, 9 | 0.386 |
| Cycle cancellation for ovarian hyper-response, n (%) | 3 (4%) | 4 (5%) | 1.000 | 0 (0%) | 1 (<1%) | — |
| Early OHSS (moderate/severe), n (%) | 3 (4%) | 4 (5%) | 1.000 | 3 (3%) | 5 (5%) | 0.727 |
| Intervention for ovarian hyper-response, n (%) | 5 (7%) | 6 (8%) | 1.000 | 7 (8%) | 12 (12%) | 0.470 |
| Oocyte retrieval | | | | | | |
| Women with oocyte retrieval, n (%) | 72 (95%) | 73 (92%) | 0.555 | 85 (98%) | 100 (99%) | 0.475 |
| Oocytes retrieved (n) | 12 (9, 16) | 15 (11, 20) | 0.007 | 12 (8, 15) | 14 (10, 19) | 0.033 |
| Women with ≥15 oocytes retrieved, n (%) | 25 (33%) | 40 (51%) | 0.025 | 27 (31%) | 49 (49%) | 0.015 |
| Fertilisation and embryo data | | | | | | |
| Fertilisation rate (%) | 50 (27, 73) | 56 (35, 69) | 0.826 | 57 (43, 69) | 60 (41, 73) | 0.663 |
| Embryos on day 3 (n) | 3 (2, 6) | 4 (2, 6) | 0.806 | | | |
| Women with top-quality embryo(s) on day 3, n (%)† | 38 (53%) | 35 (48%) | 0.561 | | | |

TABLE 2-continued

Comparison of baseline, end-of-stimulation, oocyte and embryo characteristics between HP-hMG- and rFSH-treated women with potential for being high-responders by a high AMH at start of stimulation.

| | Long GnRH agonist protocol AMH Q4: >75th (>5.2 ng/ml) | | | GnRH antagonist protocol AMH Q4: >75th (>5.2 ng/ml | | |
|---|---|---|---|---|---|---|
| Variable | HP-hMG (n = 76) | rFSH (n = 79) | p Value * | HP-hMG (n = 87) | rFSH (n = 101) | p Value * |
| Blastocysts on day 5 (n) | | | | 3 (1, 6) | 3 (1, 6) | 0.969 |
| Women with good-quality blastocyst(s) on day 5, n (%)‡ | | | | 55 (65%) | 51 (51%) | 0.060 |
| Women with transfer, n (%)¶ | 61 (85%) | 61 (84%) | 0.848 | 72 (85%) | 87 (87%) | 0.655 |

Values are median (IQR) unless otherwise indicated.
* Wilcoxon test (continuous data); Chi-Square test or Fisher's exact test (categorial data).
†Top-quality embryos were defined as 4-5 cells on day 2, ≥7 cells on day 3, equally-sized blastomeres and ≤20% fragmentation on day 3 and no multinucleation.
‡Good-quality blastocysts were defined as blastocysts with expansion and hatching score ≥4 and with inner cell mass and trophectoderm grades of A or B, using the definitions described by Gardner & Schoolcraft, supra.
¶Among women with oocytes retrieved.

The retrospective analysis revealed that HP-hMG was associated with a lower median number of oocytes retrieved in women with high AMH as compared with rFSH (long agonist protocol: −3 oocytes, p=0.007; antagonist protocol: −2 oocytes, p=0.033). In both protocols, the percentage of women with a high ovarian response was significantly lower for HP-hMG compared with rFSH (long agonist protocol: 33% versus 51%, p=0.025; antagonist protocol: 31% versus 49%, p=0.015)(see FIG. 1A). Therefore, the risk of high response was reduced with HP-hMG by 35 and 37%, respectively. There were no apparent differences between the two gonadotropin groups concerning cycle cancellations due to excessive response, early moderate/severe OHSS or interventions for excessive response in either protocol.

Within each protocol, fertilization rate, number of embryos/blastocysts available for transfer, women with top-quality embryo(s)/good-quality blastocyst(s) and percentages of women with transfer were similar between the HP-hMG and rFSH groups in the high AMH category. However, in both protocols a statistical trend (p<0.10) for improved live birth rate per started cycle was observed for HP-hMG compared with rFSH (see FIG. 1B). When restricted to women with embryo transfer, the difference in live birth rate between HP-hMG and rFSH was statistically significant (p=0.043) in the antagonist protocol.

When the data of women with high AMH from both protocols were integrated, HP-hMG treatment was associated with significantly lower incidence of high response (32% (52/163) versus 49% (89/180), p<0.001) and increased live birth rate per started cycle (34% (55/163) versus 22% (39/180), p=0.012) as well as per embryo transfer cycle (41% (55/133) versus 26% (39/148), p=0.008) compared with rFSH treatment. The logistic regression analysis (Table 3 below) indicated that the type of GnRH protocol did not explain the difference in live birth rates between HP-hMG and rFSH, as it remained significant (p=0.012) in the adjusted analysis. The probability of a live birth significantly increased with the availability of a top-quality embryo/good-quality blastocyst for transfer (p<0.001), while an increased progesterone level (p=0.042) and increased progesterone/estradiol ratio (p=0.042) at end of stimulation significantly decreased the probability of live birth (Table 3 below). However, in all adjusted analyses the difference between the two gonadotropin preparations remained significant (p<0.05) indicating that the higher live birth rate in women with high AMH and stimulated with HP-hMG could not be attributed to differences in the baseline and end-of-stimulation variables examined.

TABLE 3

Logistic regression analysis of live birth rate adjusting for baseline characteristics or end-of-stimulation variables.

| | Overall population of potential high-responders (n = 343) | |
|---|---|---|
| Variables | OR [95% CI] | P-value$^a$ |
| Adjusting for type of stimulation protocol | | |
| Antagonist protocol vs. long agonist protocol | 1.11 [0.69; 1.80] | 0.666 |
| HP-hMG vs. rFSH | 1.85 [1.14; 2.99] | 0.012 |
| Adjusting for age | | |
| Age (years) | 1.00 [0.92; 1.09] | 0.975 |
| HP-hMG vs. rFSH | 1.84 [1.14; 2.98] | 0.013 |
| Adjusting for BMI | | |
| BMI (kg/m$^2$) | 1.03 [0.92; 1.15] | 0.579 |
| HP-hMG vs. rFSH | 1.79 [1.10; 2.92] | 0.020 |
| Adjusting for menstrual cycle length | | |
| Cycle length (days) | 1.05 [0.92; 1.191] | 0.500 |
| HP-hMG vs. rFSH | 1.84 [1.14; 2.98] | 0.013 |
| Adjusting for first treatment cycle | | |
| First treatment cycle | 1.09 [0.65; 1.85] | 0.737 |
| HP-hMG vs. rFSH | 1.85 [1.14; 2.991] | 0.012 |
| Adjusting for total number of follicles on stimulation day 1 | | |
| Total number of follicles | 0.99 [0.96; 1.02] | 0.435 |
| HP-hMG vs. rFSH | 1.89 [1.16; 3.07] | 0.010 |
| Adjusting for FSH on stimulation day 1 | | |
| FSH (IU/l) | 1.10 [1.00; 1.21] | 0.060 |
| HP-hMG vs. rFSH | 1.89 [1.16; 3.06] | 0.010 |
| Adjusting for estradiol at end-of-stimulation | | |
| Estradiol (nmol/l) | 0.99 [0.96; 1.03] | 0.716 |
| HP-hMG vs. rFSH | 1.85 [1.14; 3.01] | 0.013 |
| Adjusting for progesterone at end-of-stimulation | | |
| Progesterone (nmol/l) | 0.84 [0.71; 0.99] | 0.042 |
| HP-hMG vs. rFSH | 1.76 [1.08; 2.87] | 0.024 |
| Adjusting for progesterone/estradiol at end-of-stimulation | | |
| Progesterone/estradiol | 0.26 [0.07; 0.95] | 0.042 |
| HP-hMG vs. rFSH | 1.68 [1.02; 2.75] | 0.040 |

TABLE 3-continued

Logistic regression analysis of live birth rate adjusting for baseline characteristics or end-of-stimulation variables.

| Variables | Overall population of potential high-responders (n = 343) | |
|---|---|---|
| | OR [95% CI] | P-value[a] |
| Adjusting for number of follicles ≥12 mm at end-of-stimulation | | |
| Follicles ≥12 mm | 1.05 [0.99; 1.10] | 0.094 |
| HP-hMG vs. rFSH | 1.93 [1.18; 3.16] | 0.008 |
| Adjusting for endometrial thickness at end-of-stimulation | | |
| Endometrial thickness (mm) | 0.97 [0.85; 1.10] | 0.653 |
| HP-hMG vs. rFSH | 1.84 [1.13; 2.99] | 0.014 |
| Adjusting for number of oocytes retrieved | | |
| Number of oocytes retrieved | 1.00 [0.96; 1.04] | 0.973 |
| HP-hMG vs. rFSH | 1.85 [1.13; 3.02] | 0.014 |
| Adjusting for top-quality embryo(s)/good-quality blastocyst(s) on transfer day | | |
| ≥1 Top-quality embryo/good-quality blastocyst | 2.61 [1.48; 4.61] | <0.001 |
| HP-hMG vs. rFSH | 1.80 [1.08; 3.00] | 0.025 |

OR = odds ratio;
CI = Wald confidence interval
[a]Two-sided Wald test of OR = 1 (no effect).

These results show that the prevalence of patients with a high ovarian response (i.e. ≥15 oocytes retrieved) was approximately three times higher in women with high AMH (≥5.2 ng/ml) than in women in the non-high AMH category in both the long GnRH agonist and GnRH antagonist protocol. Although women with high AMH showed ovarian hyper-response in both the antagonist and long agonist protocols, ovarian stimulation with HP-hMG was associated with a substantially lower high-response rate than stimulation with rFSH. Hence, the risk of developing a high response where an excessive response is predicted may be reduced by approximately one third by using HP-hMG instead of FSH for controlled ovarian stimulation, even in the GnRH antagonist protocol.

Without being bound by any theory, it is possible that the more moderate ovarian response with HP-hMG, and the consequently reduced risk of hyper-response with HP-hMG compared with rFSH, may be attributed at least in part to the different FSH isoform profiles of HP-hMG and rFSH, which may influence the in vivo biopotency in humans and thereby the rate of high ovarian response among the potential high-responders. Other contributing factors may be the LH activity provided by HP-hMG that is not present in rFSH, and the post-menopausal FSH isoform profile found in the FSH activity of HP-hMG.

The logistic regression analyses in the overall population did not identify any specific variable(s) that explained the different live birth rates between HP-hMG and rFSH stimulation, but indicated that progesterone levels and progesterone/estradiol ratios at the end of stimulation and the availability of top-quality embryos/good-quality blastocysts (as assessed morphologically; aneuploidy was not assessed) influenced live birth rates.

Further analysis of the results suggested to the inventors that the use of HP-hMG for controlled ovarian stimulation has a direct effect on improved oocyte quality and may reduce aneuploidy rate, and indicate that progesterone, progesterone/estradiol ratio and embryo quality play a role in treatment outcome in patients at risk of hyper-response based on high serum AMH levels.

Example 2—Prospective Clinical Trial

A randomized, assessor-blind phase IV clinical trial comparing HP-hMG and rFSH in a GnRH antagonist cycle with compulsory single-blastocyst transfer in a high responder subject population is planned for the United States. The aim of this study is to demonstrate the HP-hMG is at least non-inferior to rFSH with respect to ongoing pregnancy rate (OPR) in potential high-responders undergoing IVF/ICSI treatment. Subjects will be prospectively classified as potential high ovarian responders based on a serum level of AMH≥5.0 ng/mL by the Beckmann-Coulter Gen 2 assay as described in Arce et al., *Fertility and Sterility* 99: 1644-53 (2013), using a single reference laboratory (ReproSource, Inc., Woburn, Mass.) utilizing materials and reagents from the Beckman Coulter-DSL assay (Chaska, Minn.).

The phase IV, randomized, open-label, assessor-blind, parallel-group, multicenter study will be conducted at approximately 25-30 infertility centers in the United States. Approximately 600 females will be enrolled. Subjects are to be from age 21 up to age 36 years with regular ovulatory menstrual cycles of 21 to 35 days, with a body mass index (BMI) between 18 and 32 kg/m$^2$, or 18 and 30 kg/m$^2$, unexplained or mild male factor infertility for a period of 21 year, eligible for ICSI according to the investigator, and AMH≥5.0 ng/mL. Additional inclusion criteria may be having an AFC≥10, ≥15, ≥18, or ≥20 in both ovaries combined. Key exclusion criteria include endometriosis stage I-IV, severe male factor infertility, polycystic ovary syndrome (PCOS), and previous poor response to a COS cycle. Additional exclusion criteria may be having an AFC<8 or <10 in both ovaries combined.

Figure 2:
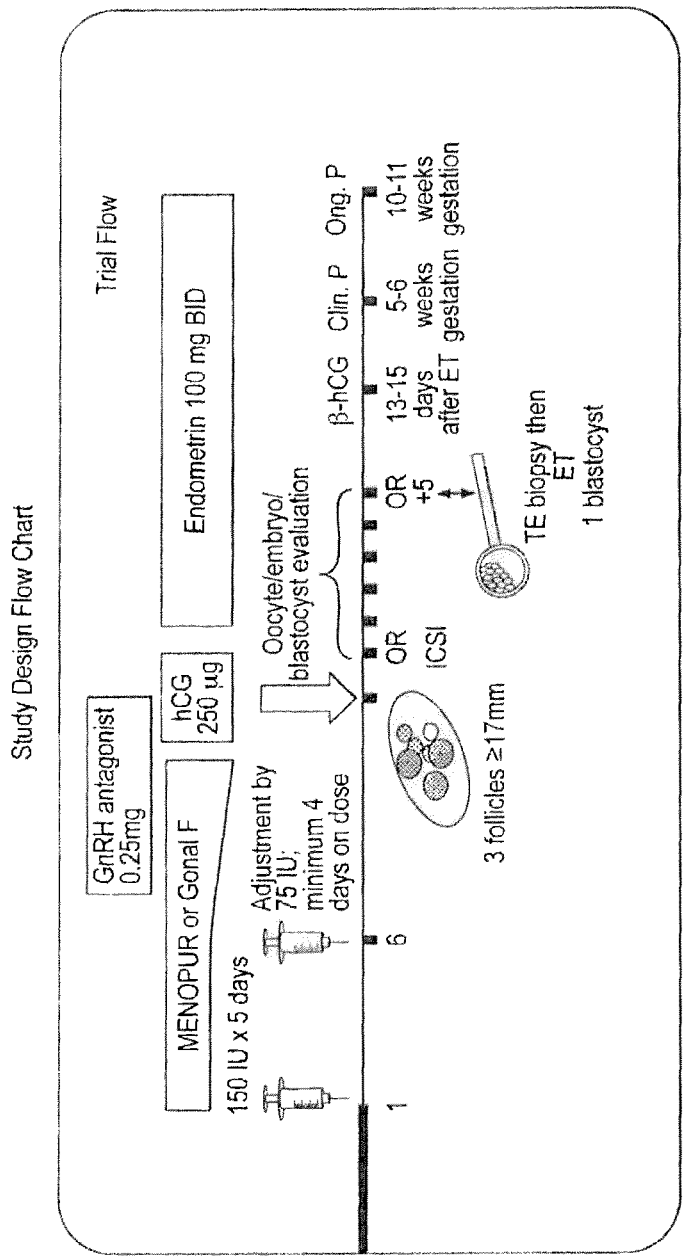
FIG. 2 sets forth a flow chart of the study design for the clinical trial of Example 2.

The basic protocol is outline in FIG. 2. Optionally, combination oral contraceptive pills (COCPs) started in the previous menstrual cycle will be continued for a maximum of 21 days. Subjects will be randomized 1:1 to undergo COS with either HP-hMG or rFSH in a GnRH antagonist cycle. After discontinuing the COCPs, gonadotropins (either HP-hMG or rFSH) will be started on the 3$^{rd}$ day of withdrawal bleeding but no sooner than the 5$^{th}$ day after discontinuation of COCPs. The gonadotropin dose will be initiated at 150 IU for the first 5 days. From Stimulation Day 6 onward, based on follicular response assessed by TVUS, dosing can be adjusted every day as needed by 75 IU per adjustment. However, the maximum gonadotropin dose will be 300 IU/day; gonadotropin dosing can continue for a maximum of 20 days. Coasting is prohibited.

When the lead follicle is >14 mm in diameter, the GnRH antagonist (ganirelix acetate) will be initiated at a daily dose of 0.25 mg and continued throughout the gonadotropin treatment period. A single injection of 250 µg hCG (choriogonadotropin alfa) will be administered to induce final follicular maturation as soon as 3 follicles of ≥17 mm diameter are observed on TVUS. If a subject has >25 follicles, she will receive a GnRH agonist trigger and all resultant blastocysts will be vitrified after trophoectoderm biopsy, with no fresh embryo transfer to decrease risk of OHSS.

Oocyte retrieval will take place roughly 36 hours after hCG administration. Oocytes will be inseminated using partner sperm by ICSI 4±1 hours after retrieval. Oocyte, embryo and blastocyst quality will be assessed daily for 5 days following oocyte retrieval. On Day 5 following ICSI, a single blastocyst of the best quality available will be transferred; all remaining blastocysts will be frozen using the vitrification method.

Trophoectoderm (TE) biopsy for preimplantation genetic screening (PGS), optionally with next generation sequencing (NGS) technology, will be done with laser on Day 5 or Day 6 of expanded blastocyst, but results will not be used to determine selection of a blastocyst for fresh transfer.

The day after oocyte retrieval, vaginal progesterone inserts (100 mg twice a day—Endometrin®; Ferring) will be initiated for luteal phase support and will continue until the day of the β-hCG test (10 to 15 days after blastocyst/embryo transfer). Luteal support may be continued until ongoing pregnancy is confirmed.

Biochemical pregnancy will be confirmed by a positive β-hCG approximately 2 weeks after blastocyst transfer. Clinical pregnancy will be confirmed by TVUS indicating at least one intrauterine gestational sac with fetal heart beat at 5 to 6 weeks gestation. Ongoing pregnancy will be confirmed by at least one intrauterine viable fetus at 10 to 11 weeks gestation.

For subjects with no ongoing pregnancy in the fresh cycle, single frozen blastocyst transfers can be initiated within 1 year of each subject's start of treatment. PGS results will be used to select the euploid blastocysts for frozen transfer. Frozen-thawed embryo replacement cycle data will be collected, including blastocyst transfer information, β-hCG test, clinical pregnancy, and ongoing pregnancy Post-trial follow-up will include collection of delivery information (live birth and neonatal health), which will be collected for all subjects with an ongoing pregnancy in the fresh cycle or the 1-year post-randomization frozen-thawed embryo replacement cycles. Live birth rate after the fresh cycle and cumulative live birth rate after fresh and 1-year post-randomization frozen-thawed embryo replacement cycles will be evaluated as part of the post-trial follow-up. The post-trial endpoints include:

Cumulative live birth rate for fresh and frozen blastocyst transfer (defined as the proportion of subjects with at least 1 viable live birth greater >21 weeks gestation);

Live birth rate for fresh blastocyst transfer (defined as the proportion of subjects with at least 1 viable live birth greater >21 weeks gestation);

Early pregnancy loss rate in frozen blastocyst transfer is defined as 2 positive β-hCG tests but no ongoing pregnancy at 10-11 weeks gestation in the frozen cycle;

Late pregnancy loss rate (defined as a confirmed ongoing pregnancy but no viable live birth greater >21 weeks gestation); and Positive β-hCG rate, clinical pregnancy rate, and ongoing pregnancy rate for frozen blastocyst transfers.

The HP-hMG used will be Menopur, provided as a vial with powder (75 IU FSH activity and 75 IU LH activity) and 2 pre-filled syringes with solvent (each containing 1.1 mL). After reconstitution, each vial delivers 75 IU of FSH activity and 75 IU of LH activity.

The FSH used will be recombinant FSH (GONAL-F), provided aspen and cartridges filled with either 300, 450 or 900 IU FSH activity/1.08 mL solution for injection.

The other drugs used will be:
Ganirelix Acetate Injection, manufactured by Merck, provided as a pre-filled syringe (0.5 mL) delivering 0.25 mg ganirelix. A daily dose of 0.25 mg will be continued throughout the gonadotropin treatment period.

Ovidrel (choriogonadotropin alfa), manufactured by EMD Serono, provided as a pre-filled syringe (0.5 mL) delivering 250 μg choriogonadotropin alfa, to be administered as a single injection as soon as 3 follicles of ≥17 mm diameter are observed on TVUS.

The primary end point is ongoing pregnancy rate in the fresh transfer cycle, defined as presence of at least one intrauterine pregnancy with a viable fetus with a detectable fetal heartbeat at 10-11 weeks gestation. Secondary endpoints include:

biochemical pregnancy rate (positive β-hCG)

clinical pregnancy rate (transvaginal ultrasonography showing at least one intrauterine gestational sac with fetal heartbeat at 5-6 weeks gestation)

Early pregnancy loss (defined as 2 positive β-hCG tests but no ongoing pregnancy at 10-11 weeks gestation in the fresh cycle.)

live birth rate follicular development endocrine profile (serum estradiol [E2], progesterone [P4], hCG, LH)

oocytes retrieved, fertilization rate, and embryo quality aneuploidy rate endometrial assessment by TVUS The present inventors believe that this study will show that stimulation of women at risk of a high ovarian response to controlled ovarian stimulation with HP-hMG improves embryo quality, increases the proportion of euploid blastocysts, decreases the proportion of aneuploid blastocysts, increases ongoing pregnancy rates and/or increases live birth rates, as compared to comparable methods using recombinant follicle stimulating hormone (rFSH) as the gonadotropin. For example, the present inventors believe that this study will show that stimulation of women at risk of a high ovarian response to controlled ovarian stimulation with HP-hMG results in fewer eggs but a higher proportion of euploid blastocysts as compared to comparable methods using rFSH as the gonadotropin.

What is claimed is:

1. A method for reducing early pregnancy loss after in vitro fertilization and transfer of a fresh or frozen blastocyst after controlled ovarian stimulation of a woman at risk of a high ovarian response to controlled ovarian stimulation, comprising:

selecting a woman at risk of a high ovarian response to controlled ovarian stimulation determined to have a serum anti-Mülllerian hormone (AMH) level greater than or equal to 5.0±0.5 ng/ml, when measured using a Beckmann-Coulter Gen 2 assay or a comparable AMH level measured by a different method; and then administering to the selected woman an amount of highly purified menotropin (HP-hMG) effective to stimulate follicle development.

2. The method of claim 1, wherein the woman has an antral follicle count (AFC) of greater than or equal to 10 in both ovaries combined, prior to stimulation.

3. The method of claim 1, wherein the woman has an antral follicle count (AFC) of greater than or equal to 15 in both ovaries combined, prior to stimulation.

4. The method of claim 1, wherein the amount of HP-hMG administered is from 100-300 IU per day for from about 1 to about 20 days.

5. The method of claim 1, wherein the amount of HP-hMG administered is from 100-200 IU per day for from about 1 to about 20 days.

6. The method of claim 1, wherein the HP-hMG is administered for at least 5 days.

7. The method of claim 1, further comprising administering a gonadotropin hormone releasing hormone (GnRH) agonist.

8. The method of claim 1, further comprising administering a gonadotropin hormone releasing hormone (GnRH) antagonist.

9. The method of claim 1, further comprising administering an amount of human chorionic gonadotropin (hCG) effective to trigger ovulation.

10. The method of claim 9, further comprising harvesting oocytes from the woman.

11. The method of claim 10, further comprising in vitro fertilization of harvested oocytes.

12. The method of claim 11, wherein the in vitro fertilization comprises intra-cytoplasmic sperm injection (ICSI).

13. The method of claim 11, further comprising assessing the chromosomal quality of blastocysts obtained from the woman after in vitro fertilization of oocytes harvested from the woman.

14. The method of claim 13, further comprising blastocyst transfer of a blastocyst determined to be a euploid blastocyst.

15. The method of claim 14, wherein the blastocyst transfer is fresh transfer.

16. The method of claim 13, further comprising freezing a blastocyst determined to be a euploid blastocyst.

17. The method of claim 1, wherein the administering comprises administering HP-hMG at a dose of 150 IU/day for at least a first 5 days of treatment.

18. A method for reducing early pregnancy loss after in vitro fertilization after controlled ovarian stimulation of a woman at risk of a high ovarian response to controlled ovarian stimulation, comprising:

selecting a woman at risk of a high ovarian response to controlled ovarian stimulation determined to have a serum anti-Müllerian hormone (AMH) level greater than or equal to 5.0±0.5 ng/ml, when measured using a Beckmann-Coulter Gen 2 assay or a comparable AMH level measured by a different method; and then administering to the selected woman an amount of highly purified menotropin (HP-hMG) effective to stimulate follicle development.

19. The method of claim 18, wherein the amount of HP-hMG administered is from 100-300 IU per day for from about 1 to about 20 days.

* * * * *